United States Patent
Sugimoto

(10) Patent No.: US 7,699,886 B2
(45) Date of Patent: Apr. 20, 2010

(54) IMPLANTABLE TUBULAR DEVICE

(75) Inventor: Ryota Sugimoto, Nakai-machi (JP)

(73) Assignee: Terumo Kabushiki Kaisha, Tokyo (JP)

( * ) Notice: Subject to any disclaimer, the term of this patent is extended or adjusted under 35 U.S.C. 154(b) by 1161 days.

(21) Appl. No.: 09/870,672

(22) Filed: Jun. 1, 2001

(65) Prior Publication Data
US 2002/0035395 A1 Mar. 21, 2002

(30) Foreign Application Priority Data
Jun. 1, 2000 (JP) .............................. 2000-164037
May 8, 2001 (JP) .............................. 2001-137449

(51) Int. Cl.
*A61F 2/06* (2006.01)
(52) U.S. Cl. ...................... 623/1.15; 623/1.46
(58) Field of Classification Search ................ 623/1.15, 623/1.11, 1.12, 23.7, 1.46, 1.16
See application file for complete search history.

(56) References Cited

U.S. PATENT DOCUMENTS

| | | | | | |
|---|---|---|---|---|---|
| 5,779,729 | A | * | 7/1998 | Severini | 128/898 |
| 5,788,979 | A | * | 8/1998 | Alt et al. | 424/400 |
| 5,876,449 | A | * | 3/1999 | Starck et al. | 623/23.7 |
| 6,063,101 | A | * | 5/2000 | Jacobsen et al. | 623/1.11 |
| 6,068,656 | A | * | 5/2000 | Von Oepen | 623/1.15 |
| 6,124,523 | A | * | 9/2000 | Banas et al. | 606/191 |
| 6,241,760 | B1 | * | 6/2001 | Jang | 623/1.12 |
| 6,251,142 | B1 | * | 6/2001 | Bernacca et al. | 427/2.24 |
| 6,254,631 | B1 | * | 7/2001 | Thompson | 623/1.15 |
| 6,254,632 | B1 | * | 7/2001 | Wu et al. | 623/1.15 |
| 6,293,967 | B1 | * | 9/2001 | Shanley | 623/1.15 |
| 6,309,414 | B1 | * | 10/2001 | Rolando et al. | 623/1.15 |
| 6,331,189 | B1 | * | 12/2001 | Wolinsky et al. | 623/1.15 |
| 6,416,543 | B1 | * | 7/2002 | Hilaire et al. | 623/1.16 |
| 6,464,720 | B2 | * | 10/2002 | Boatman et al. | 623/1.15 |
| 6,613,080 | B1 | * | 9/2003 | Lootz | 623/1.15 |
| 6,613,081 | B2 | * | 9/2003 | Kim et al. | 623/1.15 |

FOREIGN PATENT DOCUMENTS

| | | |
|---|---|---|
| EP | 0 950 386 A2 | 10/1999 |
| EP | 1 088 528 A1 | 9/2000 |
| WO | WO 99/23977 A1 | 5/1999 |
| WO | WO 01/00112 A1 | 1/2001 |

* cited by examiner

*Primary Examiner*—Fenn C Mathew
(74) *Attorney, Agent, or Firm*—Cermak Kenealy Vaidya & Nakajima LLP

(57) ABSTRACT

An implantable tubular device is formed as a substantially tubular body and has a deformable portion formed on a peripheral surface thereof, with the deformable portion forming a predetermined angle with respect to an axial direction of the implantable tubular device. The implantable tubular device includes a plurality of wavy annular members each formed of a wavy element and arranged in an axial direction of the implantable tubular device; and connection portions each connecting the wavy annular members to each other in the axial direction of the implantable tubular device. Each of the wavy annular members has a deformable portion 11 formed on a bent portion thereof not connected to the other wavy annular members in such a way that the deformable portion crosses the wavy annular member.

31 Claims, 15 Drawing Sheets

IMPLANTABLE TUBULAR DEVICE

BACKGROUND OF THE INVENTION

The present invention relates to an implantable tubular device such as a stent to be implanted in human body such as a blood vessel, a bile duct, a trachea, an esophagus, an ureter, and internal organs to improve a stenotic lesion or a total occlusion formed in the lumens.

To cure various diseases that are caused when the blood vessel or lumens are stenosis or occlusion, the stent which is a tubular-shaped medical appliance is implanted at the stenotic lesion or the total occlusion to expand them and secure the lumen thereof.

The stent is classified into a self-expandable stent and a balloon expandable stent, depending on the function thereof and an implantation method. The balloon expandable stent itself has no dilating function. After the balloon expandable stent is inserted into a target lesion, a balloon expanded inside the stent in an extent almost equal to the normal diameter of the lumen of the target lesion is inflated to dilate (plastic deformation) the stent by the inflation force of the balloon so that the stent comes in close contact with the inner surface of the target lesion.

To deliver the stent to a desired portion of a human body, it is necessary that the mounted balloon and the stent are flexible. As a method of improving the flexibility of an approximately tubular stent having a plurality of annular units disposed axially and joining portions joining adjacent annular units to each other, the method of reducing the number of joining portions (articulation) disposed between the adjacent annular units is known(i.e. mono-link stent).

However, this method is incapable of improving the flexibility of the annular unit. Therefore, there is a demand for the development of an implantable device, such as a stent to be implanted in lumens, which is flexible so that it can pass smoothly through a curve portion of the human body.

The present invention has been made to solve the above-described problem. Therefore, it is an object of the present invention to provide an implantable tubular device, for example, a stent, having a deformable portion to improve the flexibility of an annular unit of the device so that the device can pass easily through a bent portion of a human body

SUMMARY OF THE INVENTION

The object described above is attained by an implantable tubular device formed substantially tubular and having a deformable portion formed on a peripheral surface thereof, with said deformable portion forming a predetermined angle with respect to an axial direction of said device and being easy to deform in comparison with a remainder part of said device.

DESCRIPTION OF THE PREFERRED EMBODIMENTS

Figure 1:
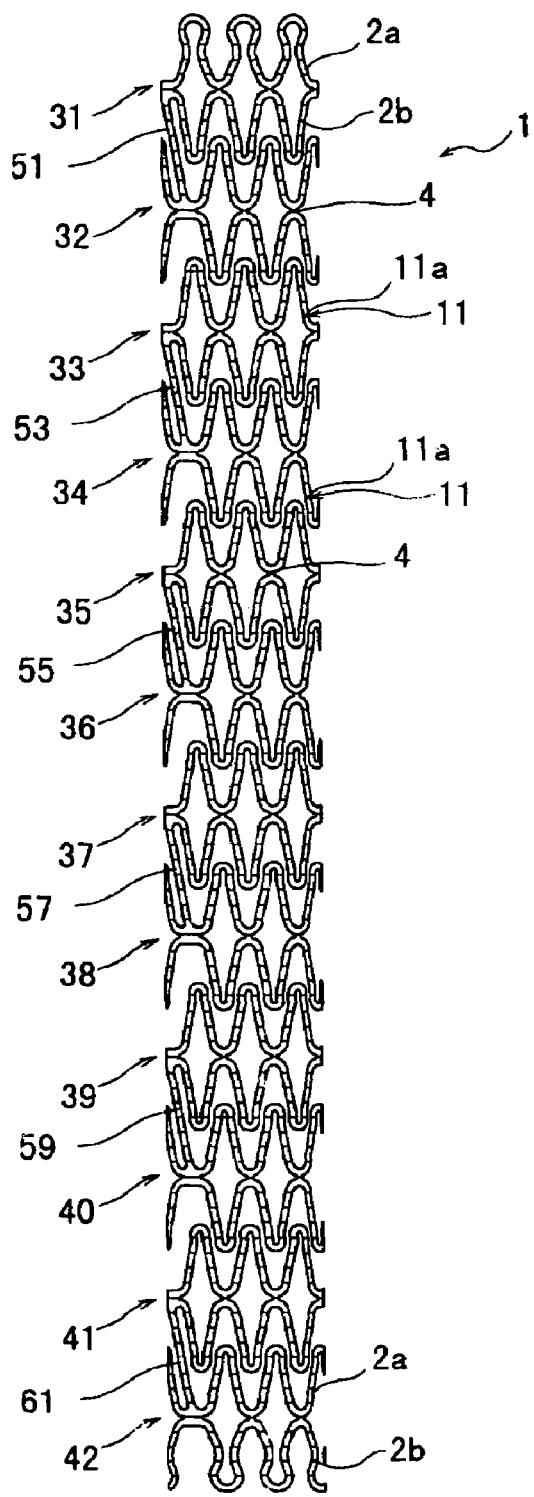
FIG. 1 is a front view of an implantable tubular device according to an embodiment of the present invention.

An embodiment of the implantable tubular device of the present invention (hereinafter referred to as mostly "device") will be described below with reference to the drawings.

An implantable tubular device 1 of the present invention to be implanted in a lumen is formed substantially tubular and has an easy deformable portion formed on a peripheral surface thereof, with the deformable portion forming a predetermined angle with respect to the axial direction of the device 1. It can be said that the deformable portion is a weak portion or a thin portion. The deformable portion is easy to deform in comparison with a remainder part of the device.

Because the implantable tubular device 1 of the present invention has the deformable portion, the implantable tubular device has a high flexibility and can pass through a bent or curved portion of a human body easily and leaves little hysteresis of deformation which occurs at the time of insertions thereof in the human body.

The implantable tubular device of the present invention to be implanted in lumens of the human body includes a stent and a stent graft that is used to improve a stenotic lesion or a total occlusion formed in the lumens such as a blood vessel, a bile duct, a trachea, an esophagus, an ureter, and the like.

The deformable portion includes a portion which is thinner than the other portion (undeformable portion) of the device and thus more flexible than the other portion; a portion which has pores and is thus more flexible than the other portion (undeformable portion) of the device; or a portion which is made of a material having a lower strength than the other portion (undeformable portion) of the device and is thus more frail than the other portion. The deformable portion of the implantable tubular device 1 shown in FIG. 1 forms a predetermined angle with respect to the axial direction of the device. Accordingly, the implantable tubular device can be curved easily along a curved portion formed in a lumen. The deformable portion is so formed that it makes a predetermined angle with respect to the axial direction of the device. In other words, the deformable portion is so formed that it is not parallel with the axial direction of the device. Therefore, when the implantable tubular device is inserted into the human body and diametrically enlarged, the deformable portion does not cause the device to be broken.

An embodiment of the implantable tubular device of the present invention will be described below with reference to FIG. 1.

The implantable tubular device of the present invention is formed as a substantial tubular body. The implantable tubular device 1 has a diameter so set that it can be inserted into a lumen in the human body and can dilate radially upon application of a force acting radially outwardly from the interior of the tubular body. The implantable tubular device has a plurality of wavy annular members each formed of a wavy element and arranged in the axial direction thereof; and connection portions each connecting the adjacent wavy annular members to each other in the axial direction thereof. The wavy annular member has the deformable portion formed on a bent portion thereof not connected to the other wavy annular members in such a way that the deformable portion crosses the wavy annular member.

In this embodiment, the implantable tubular device consists of a stent 1.

The implantable tubular device (stent) 1 is a so-called balloon expandable stent. That is, the stent 1 is formed as substantially tubular body and has a diameter so set that the stent 1 can be inserted into the human body. The stent 1 can dilate radially outwardly upon application of a force acting radially outwardly from the interior of the tubular body.

The stent 1 has a frame structure. The stent 1 of the embodiment includes annular units 31, 32, 33, 34, 35, 36, 37, 38, 39, 40, 41, and 42 each consisting of a first wavy annular member 2a annularly formed of a wavy element (preferably having no edge); a second wavy annular member 2b disposed in the axial direction of the stent 1 in such a way that a mountain thereof is proximate to a valley of the first wavy annular member 2a and annularly formed of a wavy element (preferably having no edge); and a plurality of connection portions 4 (preferably having no edge) connecting the valley of the first wavy annular member 2a and the mountain of the second wavy annular member 2b to each other. The stent 1 further includes joining portions 51, 52, 53, 54, 55, 56, 57, 58, 59, 60, and 61 (preferably having no edge) arranged in the axial direction of the stent 1 and each connecting the wavy elements (the second wavy annular member 2b and the first wavy annular member 2a) of the adjacent annular units to each other. It can be said that the stent 1 is a tubular body constructed of a plurality of annular units connected to each other with the joining portions. In the stent 1 of the embodiment, it can be also said that one annular unit is annularly formed of a plurality of rhombic elements annularly arranged.

Figure 2:
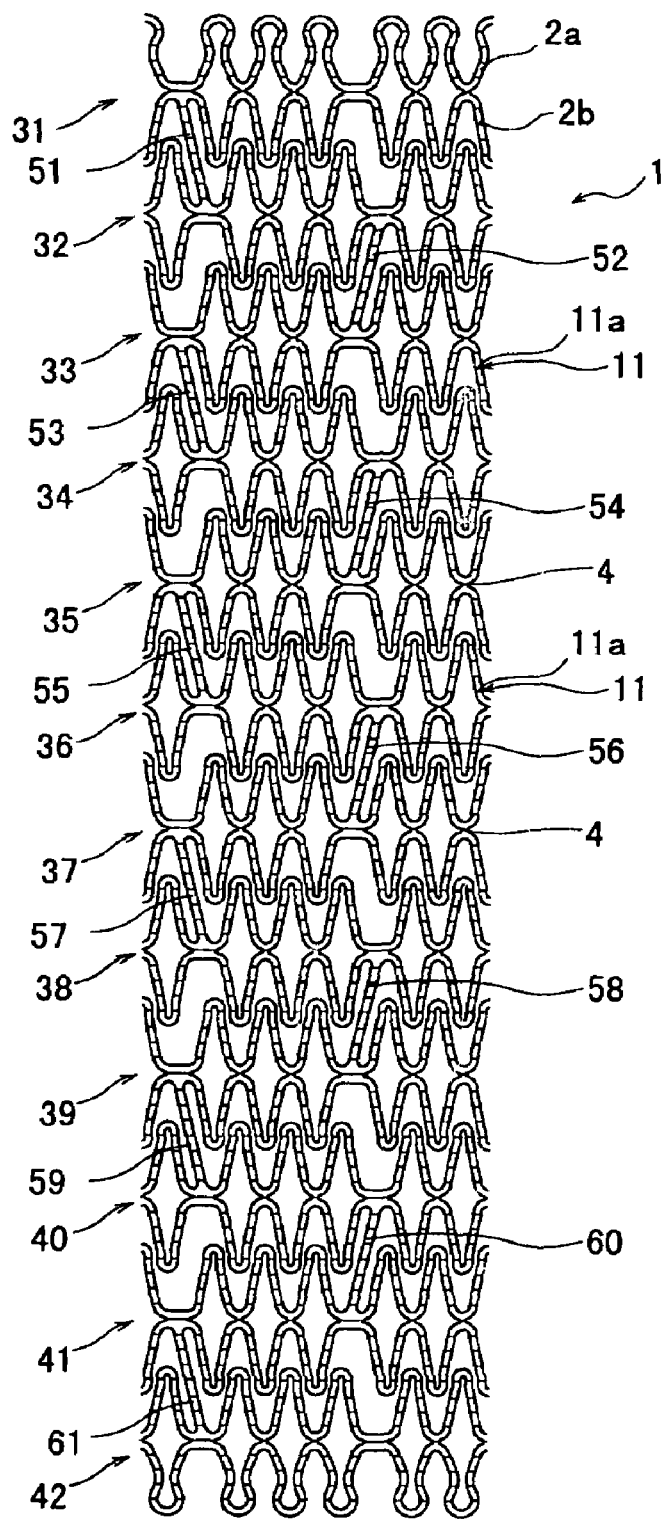
FIG. 2 is a development view of the implantable tubular device of FIG. 1.

As shown in FIG. 1 and FIG. 2 which is a developed view of FIG. 1, each of the first wavy annular member 2a and the second wavy annular member 2b is constructed of an tubularly continuous endless wavy material having six mountains and valleys. Preferably, the number of the mountains (or valleys) of the tubular bodies is four to seven. Each of a plurality of short connection portions connects the valley of the second wavy annular member and the mountain of the second wavy annular member 2b disposed in the axial direction of the stent 1 in such a way that the mountain thereof is proximate to the valley of the first wavy annular member 2a. In this manner, one annular unit is constructed. In the embodiment, the connection portions 4 connect all the valleys of the second wavy annular member and all the mountains of the second wavy annular member 2b to each other. One annular unit has six (equal to the number of mountains or valleys of the tubular body) connection portions 4.

It is preferable that the material for the stent 1 has a certain degree of compatibility with an organism. For example, it is possible to use stainless steel, tantalum or tantalum alloys, platinum or platinum alloys, gold or gold alloys, and cobalt base alloys. It is preferable to plate the stent with a noble metal such as gold and platinum after the stent is fabricated into a final shape. As the stainless steel, SUS 316L most corrosion-resistant of the above metals can be preferably used.

It is preferable to anneal the stent 1 after it is fabricated into the final shape. Annealing improves the flexibility and plasticity of the entire stent so that the stent can be effectively implanted in a curved blood vessel. As compared with a non-annealed stent, the annealed stent has a lower force of restoring to an original state after it is dilated and has a lower force of restoring to an original linear state when it is dilated at a curved portion of a blood vessel. This minimizes physical stimulation to the inner wall of the curved blood vessel, thus reducing the cause of a recurrence of stenosis. The stent is preferably annealed by heating it to 900 to 1200° C. in an inert gas atmosphere (e.g., a mixture gas of nitrogen and hydrogen) so that no oxide film is formed on the surface of the stent and then slowly cooling it.

The stent 1 has a diameter of favorably 0.8 to 1.8 mm and more favorably of 1.0 to 1.6 mm in an undilated state. The stent 1 has a length favorably of 9 to 40 mm in an undilated state The length of each of the wavy annular members 2a, 2b has a length of 0.7 to 2.0 mm. The length of each of the annular units 31 through 42 is favorably 1.5-4.0 mm and more favorably 2.0-3.0 mm. The length of each connection portion 4 is favorably 0.01-0.5 mm. The number of the annular units 31 through 42 is 3 to 50. The constituent elements (annular member) of the adjacent annular units have an axial overlap length of about 0.5 to 1 mm. The distance between the center of one annular unit and that of the annular unit adjacent thereto is preferably 1.3 to 2.5 mm. The length of each of the joining portions 51, 52, 53, 54, 55, 56, 57, 58, 59, 60, and 61 is preferably 1.4 to 2.7 mm. The angle of inclination (the angle of inclination of the joining portion with respect to the longitudinal direction of the stent in a development view) of each of the joining portions 51 through 61 with respect to the axis of the stent is favorably 0° to 30° and more favorably 50 to 25°.

The thickness of each of the wavy annular members 2a, 2b of the stent 1 and that of each of the joining portions 51, 52, 53, 54, 55, 56, 57, 58, 59, 60, and 61 are favorably 0.05 to 0.15 mm and more favorably 0.08 to 0.12 mm. The width of each of the wavy annular members 2a, 2b and that of each of the joining portions 51, 52, 53, 54, 55, 56, 57, and 58 are favorably 0.07 to 0.15 mm and more favorably 0.08 to 0.12 mm. The thickness of the connection portion 4 of the stent 1 is favorably 0.05-0.12 mm and more favorably 0.06-0.10 mm. The width of the connection portion 4 of the stent 1 is favorably 0.01-0.05 mm and more favorably 0.02 to 0.04 mm. The sectional area of the connection portion 4 is favorably $\frac{1}{50}$ to $\frac{1}{2}$ of that of the other parts (annular member and joining portion) and more favorably $\frac{1}{20}$ to $\frac{1}{10}$ of that of the other parts.

The stent 1 has the deformable portion formed on the wavy annular member constructing the stent 1. More specifically, the deformable portion is formed on a bent portion of the wavy annular member not connected to the other wavy annular members in such a way that the deformable portion crosses the wavy annular member. Therefore, the free bent portion of the wavy annular member not connected to the other wavy annular members is allowed to deform easily. Further, a deformation hysteresis that occurs when the stent 1 is inserted into the human body does not remain in the free bent portion. The deformable portion is entirely formed on the stent 1 to deform the entire stent easily.

The deformable portion is formed on the bent portion of the wavy annular member not connected to the other wavy annular members in such a way that the deformable portion crosses the wavy annular member. More specifically, when the deformable portion is viewed in the axial direction of the wavy annular member, namely, in the axial direction of the stent (device), the deformable portion is formed on the bent portion of the wavy annular member not connected to the other wavy annular members in such a way that the deformable portion crosses the wavy annular member. That is, the deformable portion forms 20-90° and favorably 70-90° with the axial direction of the device. In the embodiment, the deformable portion is almost orthogonal (90°) to the axial direction of the device.

The deformable portion is formed in such a way that when the deformable portion is prolonged, it continuously goes around the periphery of the device. That is, when the deformable portion is prolonged, it forms an endless annular configuration. Further the deformable portions are formed on the bent portion of the wavy annular member in such a way that they are substantially parallel with one another. Thereby the implantable tubular device has substantially annular grooves. Thus the implantable tubular device is prevented from being bent in a particular direction. That is, the implantable tubular device is capable of easily flexing in any directions.

The depth of a groove 11a is not definite but different according to the diameter and thickness of the stent. The depth of the groove 11a is favorably 5-50% of the thickness of the device and more favorably 10-20% thereof. The width of the groove 11a is favorably 1 μm-100 μm and more favorably 5 μm-50 μm. It is preferable that the interval between the adjacent deformable portions (the interval between the grooves, namely, the interval between the grooves in the axial direction of stent) is much shorter than the axial length of the annular unit. Thus it is preferable that the interval between the adjacent deformable portions is ⅟₈₀-⅛ of the axial length of the annular unit to improve the flexibility of the annular unit. In the case of the stent 1 of the embodiment, the interval between the adjacent grooves of the stent 1 is favorably 0.01-1 mm and more favorably 0.05-0.5 mm. The deformable portions (groove 11a) 11 of the stent 1 of the embodiment are formed at regular intervals but may be formed at irregular intervals or at regular intervals in one region and at irregular intervals in other region.

The interval between the adjacent grooves in the axial direction of the stent does not necessarily have to be uniform. For example, the interval between the adjacent grooves at both axial ends of the stent 1 may be different from that between the adjacent grooves at the axial central portion thereof to vary the flexibility of the stent 1, depending on a portion thereof. More specifically, the interval between the adjacent grooves may be short at both axial ends of the stent 1 and long at the axial central portion thereof to allow both axial ends of the stent 1 to be more flexible than the axial central portion thereof.

The groove 11a of the embodiment is formed on only the outer surface of the stent (device) 1. But the groove 11a may be formed on only the inner surface thereof or on both the outer and inner surfaces thereof. In the case where the groove 11a is formed on both the outer and inner surfaces of the substantially tubular body, it is not preferable to form the grooves on concentric circles of the tubular body to prevent the groove formed on the outer surface thereof and the groove formed on the inner surface thereof from being coincident with each other in the axial direction of the tubular body. Thereby the deformable portion does not cause a low-strength portion to be formed on the device.

The implantable tubular device (stent) is formed as a frame structure by removing a portion of a tubular body (metal pipe) other than a portion thereof which is to be formed as a frame structure. For example, the stent is formed by removing an unnecessary portion from a metal pipe by using an etching process, known as photo-fabrication, using a mask and chemicals; electric discharge machining; mechanical machining using a die; or laser machining method. After the frame structure is prepared, it is preferable to polish the edge of the frame structure by using chemical polishing or electro-polishing.

The method of processing the groove 11a (deformable portion 11) will be described below.

The groove 11a may be formed after a cylindrical member formed from the above-described forming material is processed into the shape of the stent; before the cylindrical member is processed into the shape of the stent; or at the time when the cylindrical member is processed into the shape of the stent. The groove 11a is formed by laser processing method of processing the groove by emitting laser to the cylindrical member, etching method using photoresist technique or mechanical machining. After the groove 11a is formed, it is preferable to polish the surface of the groove by using chemical polishing or electro-polishing.

In the case where the groove is formed on the inner surface of the stent 1 (in the case where the deformable portion is formed from the inner surface of the stent 1), it is preferable to use a method of forming a thread groove on the inner surface of the cylindrical member by using a tap.

In the above embodiment, the annular units are connected with each other with one joining portion, i.e., the stent of mono-link type has been exemplified. But the annular units may be connected with each other with a plurality of joining portions. That is, the stent of the present invention may be of link type.

The deformable portion does not necessarily have to consist of the groove but may consist of a thin portion having a predetermined width.

Another embodiment of the implantable tubular device of the present invention will be described below.

Figure 4:
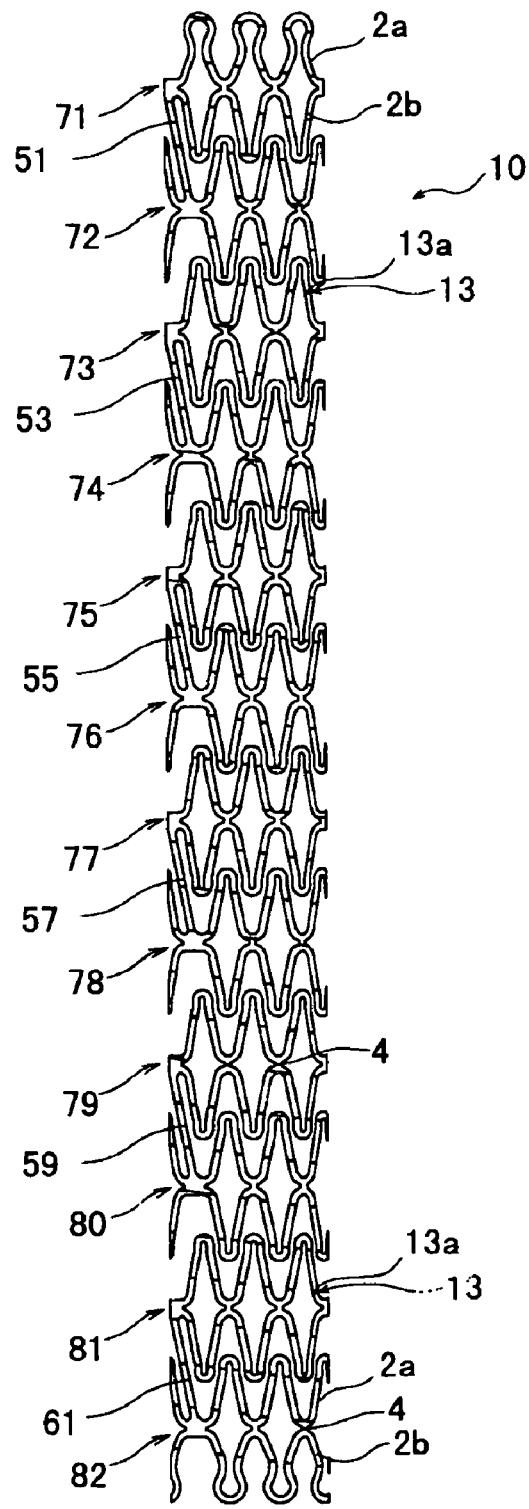
FIG. 4 is a front view of an implantable tubular device according to another embodiment of the present invention.
Figure 5:
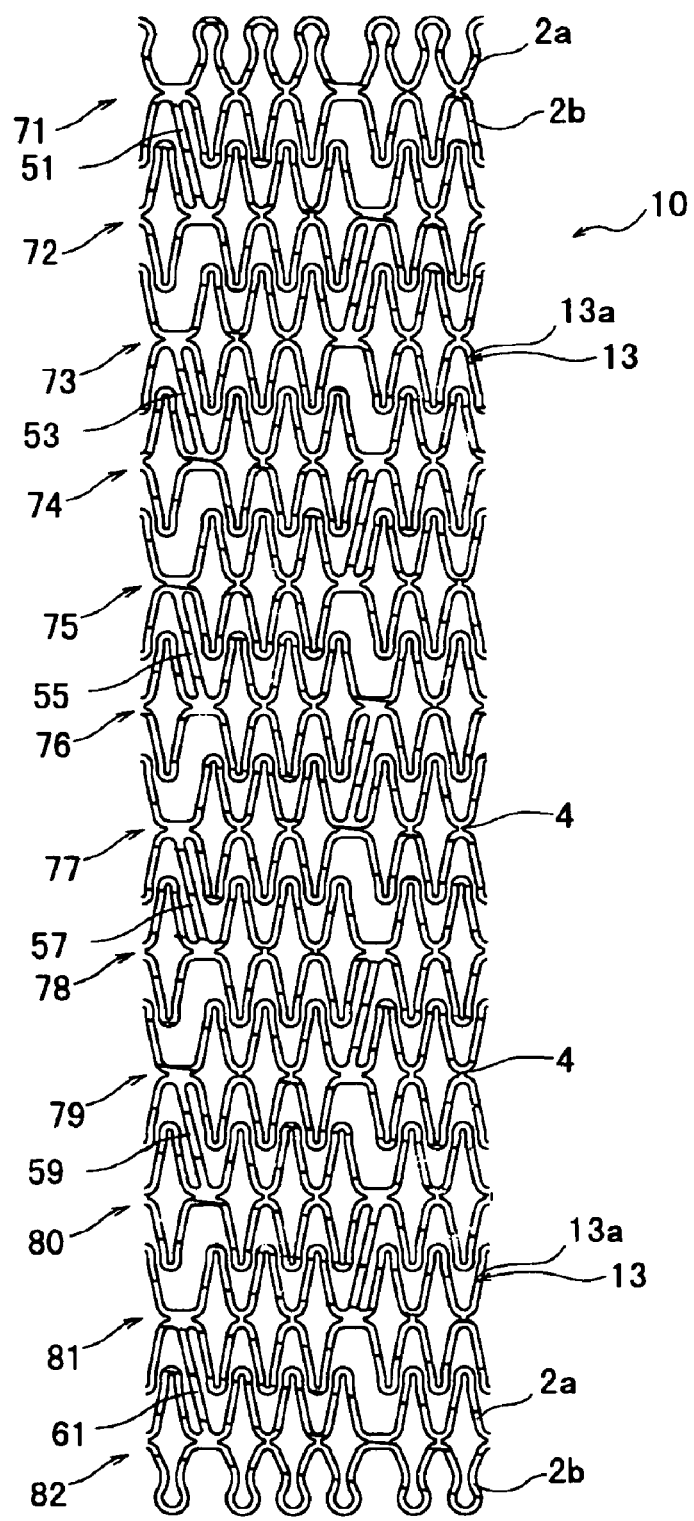
FIG. 5 is a development view of the implantable tubular device of FIG. 4.
Figure 6:
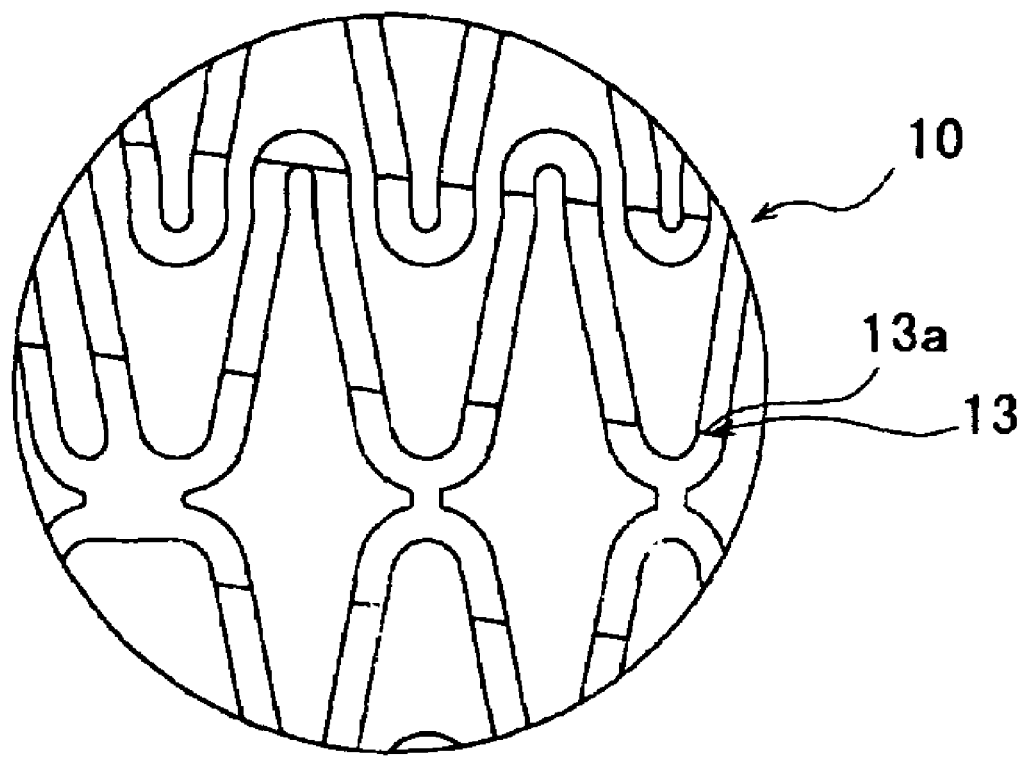
FIG. 6 is a partly enlarged front view of the implantable tubular device of FIG. 4.

FIG. 4 is a front view of a stent according to another embodiment of the present invention. FIG. 5 is a development view of the stent of FIG. 4. FIG. 6 is a partly enlarged front view of the stent of FIG. 4.

The implantable tubular device of this embodiment is different from the above-described embodiment in that a stent 10 and a deformable portion 13 of this embodiment are different from the stent 1 and the deformable portion 11 of the above-described embodiment respectively.

In the stent 10, the deformable portion 13 is so formed that when the deformable portion is prolonged, a spiral is formed on the peripheral surface of the device. Preferably, the number of spirals is 1-500. In this embodiment, the number of spirals is 34. When a plurality of spirals are formed, the interval between adjacent spirals (grooves) in the axial direction of the stent is preferably 0.05-0.5 mm. The inclination of the spiral with respect to the axial direction of the stent is preferably 60-80°.

The depth of a groove 13a is not definite but different according to the diameter and thickness of the stent. The depth of the groove 13a is favorably 5-50% of the thickness of the device and more favorably 10-20% thereof. The width of the groove 13a is favorably 1 µm-100 µm and more favorably 5 µm-10 µm.

The inclination of the spiral formed by the groove with respect to the axial direction of the stent, in other words, the pitch between the adjacent spirals formed by the groove does not necessarily have to be equal to each other. For example, the pitch between the adjacent spirals at both axial ends of the stent 10 may be different from that between the adjacent spirals at the axial central portion thereof to vary the flexibility of the stent 10, depending on a portion thereof. More specifically, the pitch between the adjacent spirals may be short at both axial ends of the stent 10 and long at the axial central portion thereof to allow both ends of the stent 10 to be more flexible than the axial central portion thereof.

The groove 13a of the present invention is formed on only the outer surface of the stent (device) 10. But the groove 13a may be formed on only the inner surface thereof or on both the outer and inner surfaces thereof. In the case where the groove 13a is formed on both the outer and inner surfaces of the substantially tubular body, it is preferable to prevent the groove formed on the outer surface thereof and the groove formed on the inner surface thereof from being coincident with each other in the axial direction of the tubular body. Thereby the deformable portion does not cause a low-strength portion to be formed on the device. The deformable portion does not necessarily have to consist of the groove but may consist of a thin portion having a predetermined width.

The deformable portion 13 of the stent 10 can be formed by the methods that are used to form the above-described deformable portion 11 of the stent 1.

In addition, the implantable tubular device of the present invention may be produced from a spiral deformable portion-provided tubular body formed by connecting axially adjacent coiled wire members to each other directly or indirectly. In this case, the implantable tubular device of the present invention is formed as a frame structure by removing a portion of the prepared tubular body other than a portion thereof which is to be formed as the device.

Figure 7:
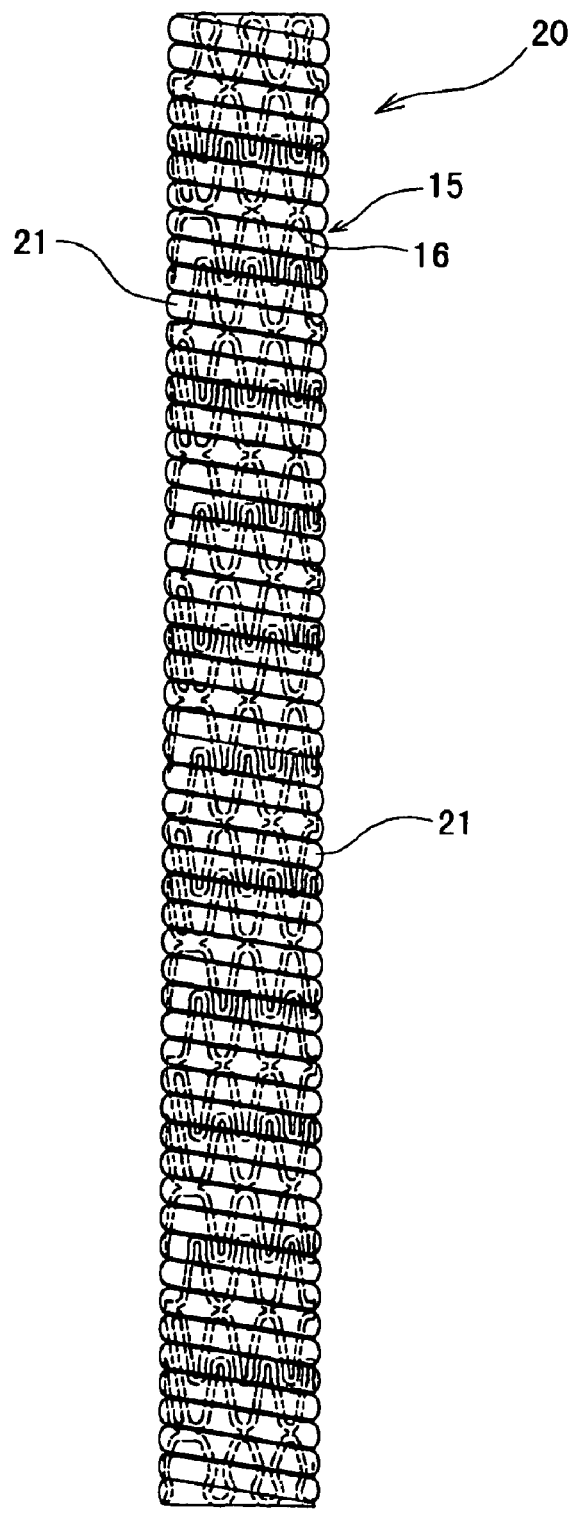
FIG. 7 is an explanatory view for describing an implantable tubular device of another embodiment of the present invention.

FIG. 7 shows the tubular body, composed of the coiled wire member, which is used as the device of the present invention with solid lines. FIG. 7 also shows the frame structure formed by removing the portion of the tubular body other than the portion thereof which is to be formed as the implantable tubular device with broken lines.

The tubular body is produced by directly or indirectly connecting adjacent coiled wire members 21 to each other in the axial direction of the coil. The tubular body has the spiral deformable portions 15.

The thickness of a connection portion 16 of the tubular body 20 is formed smaller than the diameter of the wire member 21 to deform the connection portion 16 more easily than the body of the wire member 21. The wire members 21 adjacent to each other in the axial direction of the coil may be connected to each other directly (direct connection) by welding or the like or indirectly (indirect connection) through other member having a high flexibility. In the direct and indirect connections, the entire adjacent surfaces of the wire members 21 do not necessarily have to be connected to each other but a part of the adjacent surfaces thereof can be connected to each other.

The thickness of the deformable portion 15 does not necessarily have to be smaller than the diameter of the wire member 21, provided that the implantable tubular device can deform (flex) easily, with the deformable portion acting as the point of origin of the deformation. For example, the thickness of the deformable portion 15 may be almost equal to the diameter of the wire member 21 by interposing other member between the adjacent wire members 21.

The tubular body 20 has a diameter favorably 0.8 mm to 1.8 mm and more favorably 1.0 mm to 1.6 mm. The axial length of the tubular body is favorably 3 mm to 50 mm and more favorably 5 mm-30 mm.

The wire member has a diameter favorably 0.01 to 0.2 mm and more favorably 0.05 to 0.1 mm. The interval between the adjacent wire members is favorably 0 to 0.5 mm and more favorably 0-0.1 mm. It is preferable to make the wire member of a material similar to the material for the stent 1.

As the method of shaping the implantable tubular device, in other words, as the method of producing the frame structure by removing the portion of the prepared tubular body other than the portion thereof which is to be formed as the device, etching method known as photo-fabrication, using a mask and chemicals; electric discharge machining using a die; mechanical machining or laser processing method can be used.

The implantable tubular device of this embodiment can be easily bent from the deformable portion which is formed at the connection portion of the adjacent wire members 21. Thus the implantable tubular device can pass smoothly through a bent portion of the human body.

Further the implantable tubular device of the present invention may be produced from an annular deformable portions-provided tubular body formed by directly or indirectly connecting ring members so disposed parallel to each other as to form a cylindrical shape. In this case, the implantable tubular device of the present invention is formed as a frame structure by removing a portion of the prepared tubular body other than a portion thereof which is to be formed as the device.

Figure 8:
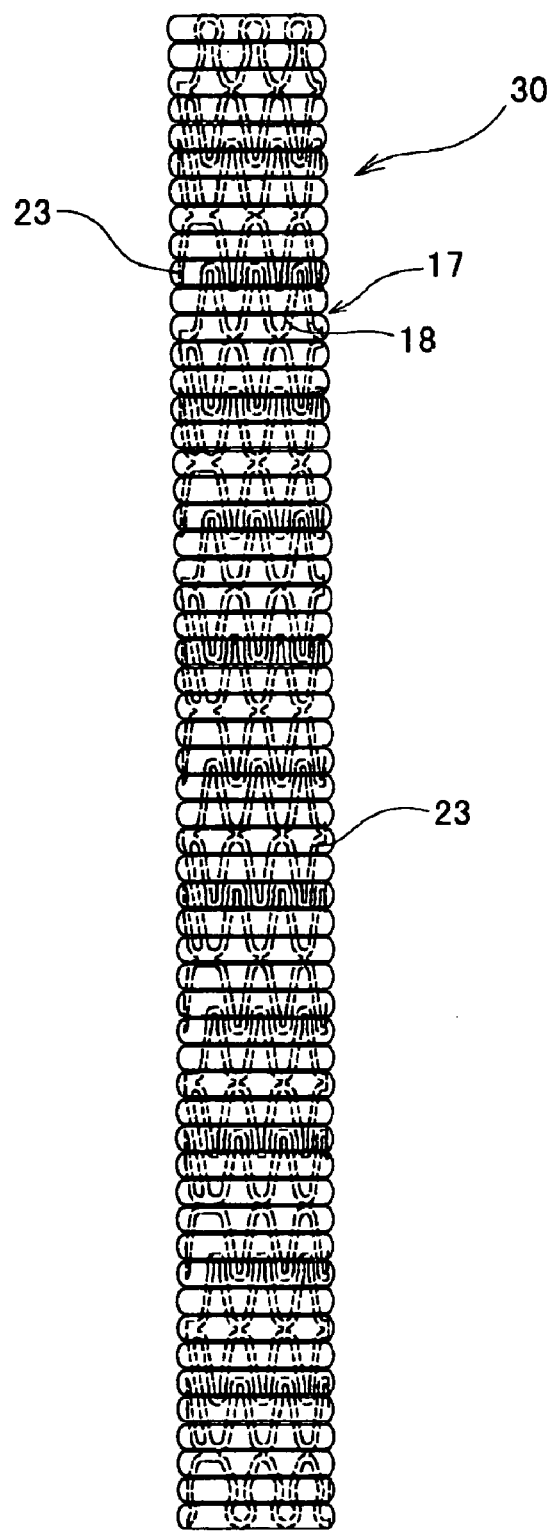
FIG. 8 is an explanatory view for describing an implantable tubular device of still another embodiment of the present invention.

FIG. 8 shows the tubular body, composed of a plurality of ring members, which is used as the implantable tubular device of the present invention with solid lines. FIG. 8 also shows a frame structure formed by removing the portion of the prepared tubular body other than the portion thereof that is to be formed as the implantable tubular device with broken lines.

The tubular body 30 is produced by directly or indirectly connecting a plurality of ring members 23 disposed parallel with one another. The tubular body 30 has a plurality of annular deformable portions 17 formed between the adjacent ring members 23. A plurality of the deformable portion 17 are formed in connection portions 18 of the adjacent ring members 23 by connecting the ring members 23 to each other in the axial direction of a stent 30. Each deformable portion 17 is endless and annular.

The ring members 23 adjacent to each other in the axial direction of the stent may be connected to each other directly (direct connection) by welding or the like or indirectly (indirect connection) through other member having a high flexibility. In the direct and indirect connections, the entire adjacent surfaces of the ring members 23 do not necessarily have to be connected to each other but a part of the adjacent surfaces thereof can be connected to each other.

The thickness of the deformable portion 17 does not necessarily have to be smaller than the diameter of the ring member 23, provided that the implantable tubular device can deform (flex) easily, with the deformable portion acting as the point of origin of the deformation. For example, the thickness of the deformable portion 17 may be almost equal to the diameter of the ring member 23 by interposing other member between the adjacent ring members 23.

The tubular body 30 has a diameter favorably 0.8 to 1.8 mm and more favorably 1.0 to 1.6 mm. The axial length of the tubular body is favorably 3 to 50 mm and more favorably 5-30 mm.

A wire material forming the ring member 23 has a diameter favorably 0.01 to 0.2 mm and more favorably 0.05 to 0.1 mm. The interval between the adjacent ring members is favorably 0 to 0.5 mm and more favorably 0-0.1 mm. It is preferable to make the ring member of a material similar to the material for the stent 1.

As the method of shaping the implantable tubular device, in other words, as the method of producing the frame structure by removing the portion of the prepared tubular body other than the portion thereof which is to be formed as the device, etching method known as photo-fabrication, using a mask and chemicals; electric discharge machining using a die; mechanical machining or laser processing method can be used.

The implantable tubular device of this embodiment can be easily bent from the deformable portion which is formed at the connection portion of the adjacent ring members 23. Thus the implantable tubular device can pass through a bent portion of the human body.

The balloon expandable stent has been described in the embodiment. But the present invention is applicable to the self-expandable stent.

The implantable tubular device may carry a medicine or a bioprosthetic material(in other words, material originated inorganism or biosynthesis material). At least one part of the outer surface of the device may be coated with a coating material made of a biocompatible material, a biodegradable material or synthetic resin. At least the outer surface of the deformable portion may be entirely coated with the coating material made of the biocompatible material, the biodegradable material or the synthetic resin.

Figure 10:
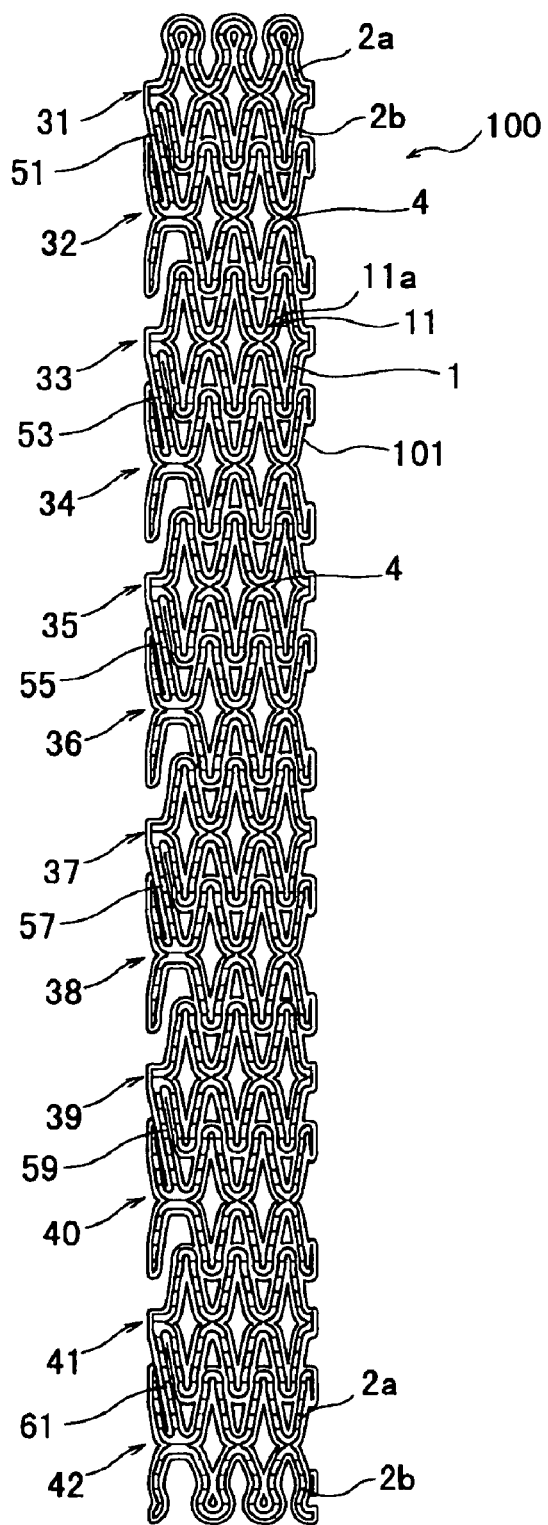
FIG. 10 is a front view of an implantable tubular device according to still another embodiment of the present invention.
Figure 11:
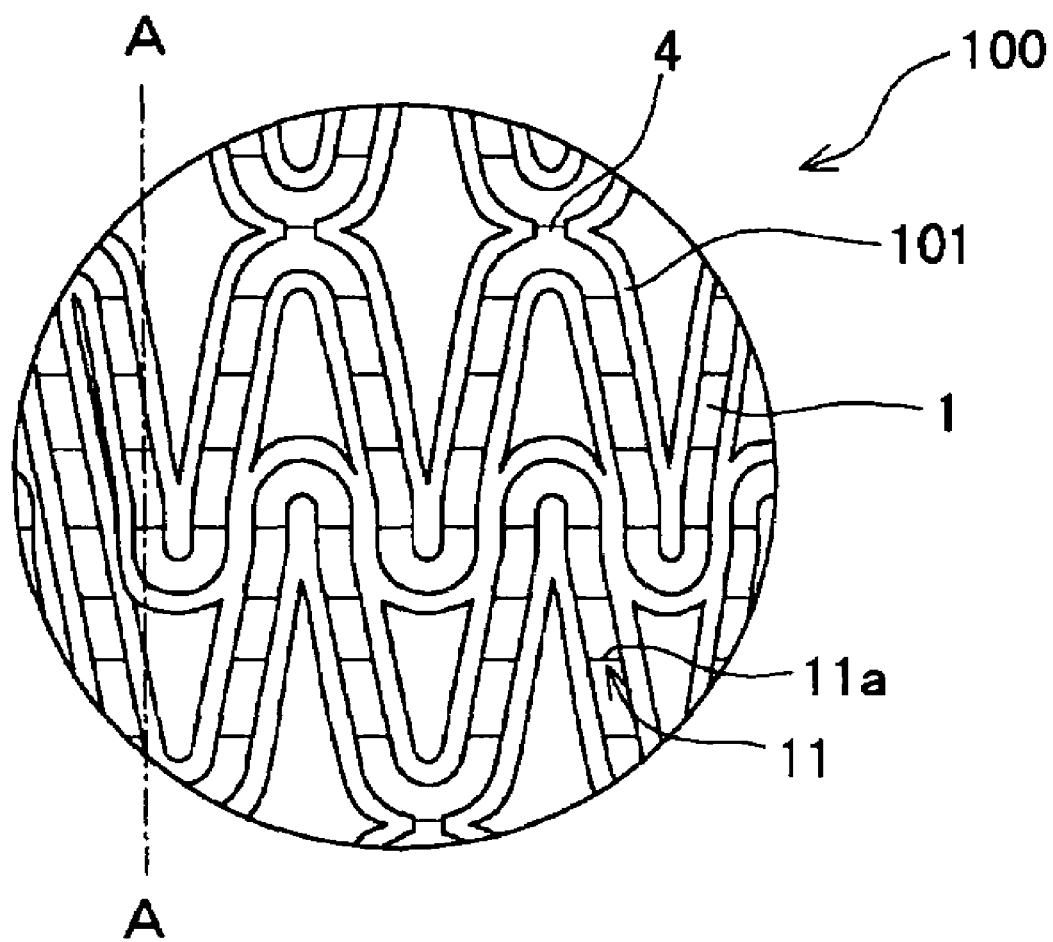
FIG. 11 is a partly enlarged view of the implantable tubular device shown in FIG. 10.
Figure 12:
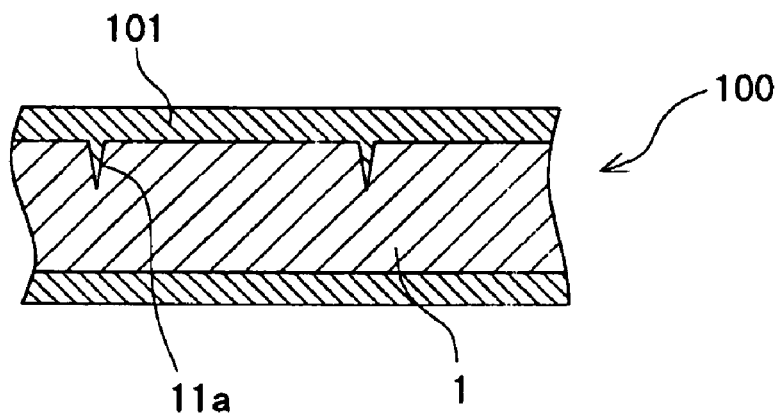
FIG. 12 is a sectional view taken along a line A-A of FIG. 11.

FIG. 10 is a front view of an implantable device according to still another embodiment of the present invention. FIG. 11 is a partly enlarged view of the device shown in FIG. 10. FIG. 12 is a sectional view taken along a line A-A of FIG. 11.

An implantable device 100 of the embodiment has a body 1 and a coating material 101 coating the implantable tubular device.

The body 1 of the implantable tubular device of the present invention is formed as a substantial tubular body and has a deformable portion formed on a peripheral surface thereof, with the deformable portion forming a predetermined angle with the axial direction of the device. At least one part of the outer surface of the implantable tubular device of this embodiment is coated with a coating material made of an biocompatible material, an biodegradable material or synthetic resin. Further At least the outer surface of the deformable portion is entirely coated with the coating material made of the biocompatible material, the biodegradable material or the synthetic resin. More specifically, the entire device is coated with the coating material made of the biocompatible material, the biodegradable material or the synthetic resin.

The body of the implantable tubular device 1 is formed as a substantial tubular body. The body of the implantable tubular device 1 has a diameter so set that it can be inserted into a lumen in the human body and can dilate radially upon application of a force acting radially outwardly from the interior of the tubular body. The body of the implantable tubular device has a plurality of wavy annular members each formed of a wavy element and arranged in the axial direction thereof; and connection portions each connecting the adjacent wavy annular members to each other in the axial direction thereof. The wavy annular member has the deformable portion formed on a bent portion thereof not connected to the other wavy annular members in such a way that the deformable portion crosses the wavy annular member.

As the body 1 of the implantable tubular device, the implantable tubular device of all of the above-described embodiments can be used. In the implantable tubular device of the embodiment, the depth of the groove 11a forming the deformable portion is not definite but different according to the diameter and thickness of the stent. The depth of the groove 11a is favorably 1-99% of the thickness of the device and more favorably 5-50% thereof.

As shown in FIGS. 10 and 12, the implantable tubular device of this embodiment has a coating material formed on the body thereof.

It is preferable that the coating material 101 coats the entire surface (outer surface and inner surface) of the body 1 of the device. But the coating material 101 may coat a part of the outer surface of the body 1 or only the outer surface of the deformable portion.

The coating material 101 consists of the biocompatible material, the biodegradable material or the synthetic resin.

The following synthetic resins can be used to form the coating material 101: ethylene-vinyl acetate copolymer, polyester, silicone rubber (RTV rubber), thermoplastic polyurethane, fluorine resin (for example, PTFE, ETFE, thermoplastic fluorine resin), polyolefin (for example, polyethylene, polypropylene, low-density polyethylene, low-density polypropylene), polyester, polycaprolactone, polyvinyl acetate, polycarbonate, polyimide carbonate, aliphatic polycarbonate, and mixtures thereof.

The following biocompatible materials can be used to form the coating material 101, provided that platelets do not attach thereto easily and that they do not stimulate tissue: saccharide, silicone, mixture or block copolymer of polyether-type polyurethane and dimethyl silicon, polyurethane such as segmented polyurethane, polyacrylamide, polyethylene oxide, polyethylene carbonate, polycarbonate such as polypropylene carbonate, polymethoxy ethyl acrylate, polyhydroxy ethyl methacrylate, copolymer of hydroxy ethyl methacrylate and styrene (for example, HEMA-St-HEMA block copolymer), and fibrin.

The following biodegradable materials can be used to form the coating material 101, provided that they are decomposed enzymatically or non-enzymatically and a decomposed matter is not poisonous: polylactic acid, polyglicolic acid, polylactic acid-polyglicolic acid copolymer, polycaprolactone, polylactic acid-polycaprolactone copolymer, polyhydroxybutyric acid, polymalic acid, poly α-amino acid, collagen, gelatin, laminin, heparan sulfate, fibronectin, vitronectin, chondroitin sulfate, hyaluronic acid, chitin, and chitosan.

The deformable portion can be reinforced with the coating material 101 coating at least the outer surface of the deformable portion 11. Further even though the body 1 of the device is broken at the deformable portion 11, the coating material prevents a broken portion from separating from the body 1.

The thickness of the coating material 101 is favorably 0.1-100 μm and more favorably 5 μm -50 μm, although its thickness is different according to the coating material that is used.

The coating material is formed on the body of the device by preparing a solution in which a solvent dissolving a coating material-forming material therein without modifying it, bringing a portion of the body of the device on which the coating material is to be formed into contact with the solution, and removing the solvent. The body of the device can be brought into contact with the solution by immersing the body in the solution or applying the solution to the body.

Figure 13:
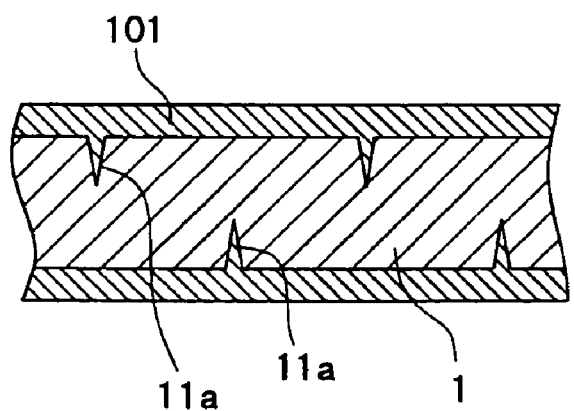
FIG. 13 is an explanatory view for describing an implantable tubular device according to still another embodiment of the present invention.

The implantable tubular device 100 shown in FIGS. 10 and 11 has the coating material 101 coating the outer surface including the outer surface of the deformable portion 11 of the body 1 of the device and the inner surface of the body 1 thereof. As the material for the coating material, those described above can be used. In the implantable tubular device 100 of the embodiment, as shown in FIG. 12, the coating material-forming material fills into the groove 11a forming the deformable portion 11. The coating material-forming material filled into the groove 11a allows the deformable portion to be reinforced without preventing a large amount of deformation of the deformable portion and also allows the coating material to adhere to the body 1 of the device firmly Thus it is possible to prevent the coating material from separating from the body 1. Furthermore because the portion of the coating material 101 filling into the groove is thicker than other portions of the coating material 101. Therefore, if the body 1 of the device is broken at the deformable portion 11 (groove 11a) in an implanting operation, the coating member is hardly broken. Thus even though the deformable portion 11 is broken, it is possible to prevent a broken portion from separating from the body 1. As shown in FIG. 13, the implantable tubular device having the groove 11a forming the deformable portion on the outer and inner surfaces of the body thereof may be used. In this case, as shown in FIG. 13, it is preferable to penetrate the coating material-forming material into the groove 11a forming the deformable portion on the outer and inner surfaces of the body of the device.

As described above, the body of the implantable tubular device is allowed to undergo a preferable deformation in the case where the body has the groove 11a forming the deformable portion on the outer and inner surfaces of the body. Further the penetration of the coating material-forming material into the groove 11a allows the deformable portion to be reinforced without preventing a large amount of the deformation of the deformable portion and also allows the coating material to adhere to the body 1 of the device firmly. Thus it is possible to prevent the coating material from separating from the body 1. Furthermore because the portion of the coating material 101 into which the coating material-forming material penetrates is thicker than other portions of the coating material 101. Therefore, if the body 1 of the implantable tubular device is broken at the deformable portion 11 (groove 11a) in an implanting operation, the coating member is hardly broken.

The body of the implantable tubular device may carry a medicine or a bioprosthetic material(in other words, biosynthesis material, material originated inorganism). As the mode of carrying the medicine or the bioprosthetic material(in other words, material originated inorganism), it is preferable that the implantable tubular device has the coating material carrying the medicine or the bioprosthetic material(in other words, material originated inorganism). But it is possible that the implantable tubular device does not have the coating material and instead carries the medicine or the bioprosthetic material(in other words, material originated inorganism) directly. As the mode of allowing the coating material to carry the medicine or the bioprosthetic material(in other words, material originated inorganism), the medicine or the bioprosthetic material(in other words, material originated inorganism) is contained in the layer of the coating material or applied to the surface thereof. The coating material may be porous.

As a favorable mode, a mixture of the medicine and the biodegradable material is essentially applied to the outer surface of the body of the device. As a more favorable mode, the mixture of the medicine and the biodegradable material is applied to the entire surface thereof. By doing so, after the implantable tubular device is implanted in the human body, the biodegradable material decomposes and the medicine is gradually discharged from the coating material. Thereby the effect of the medicine can be obtained continuously for a certain period of time.

Figure 14:
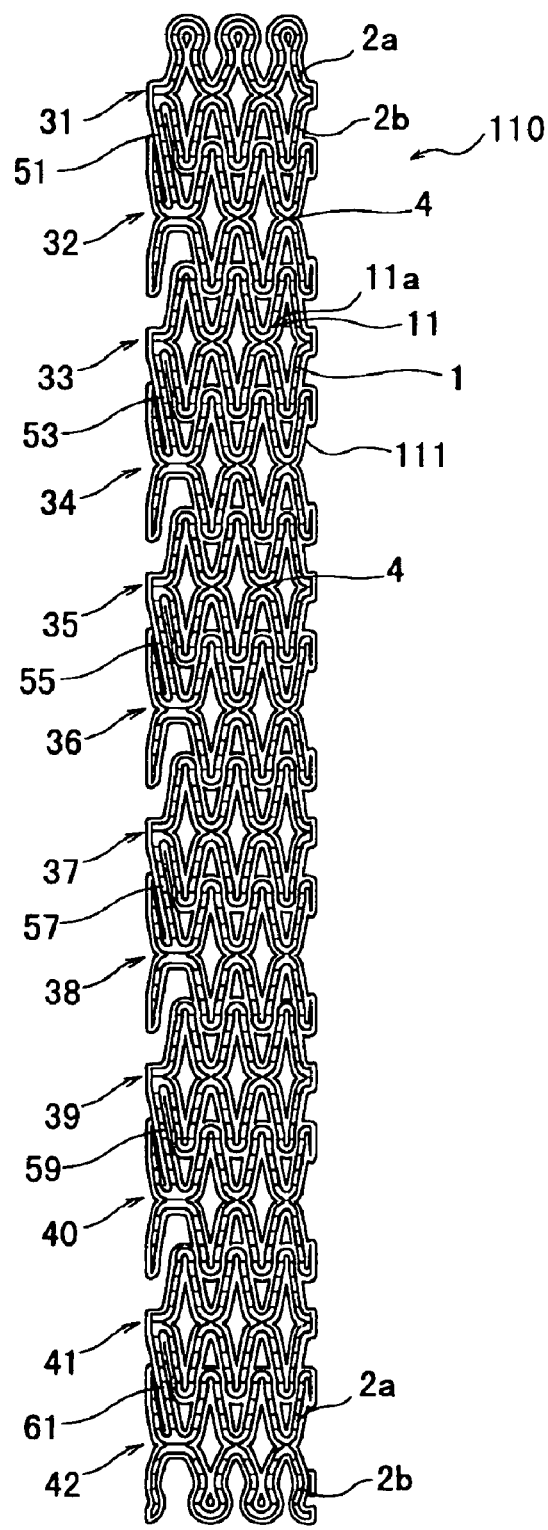
FIG. 14 is a front view of an implantable tubular device according to still another embodiment of the present invention.
Figure 15:
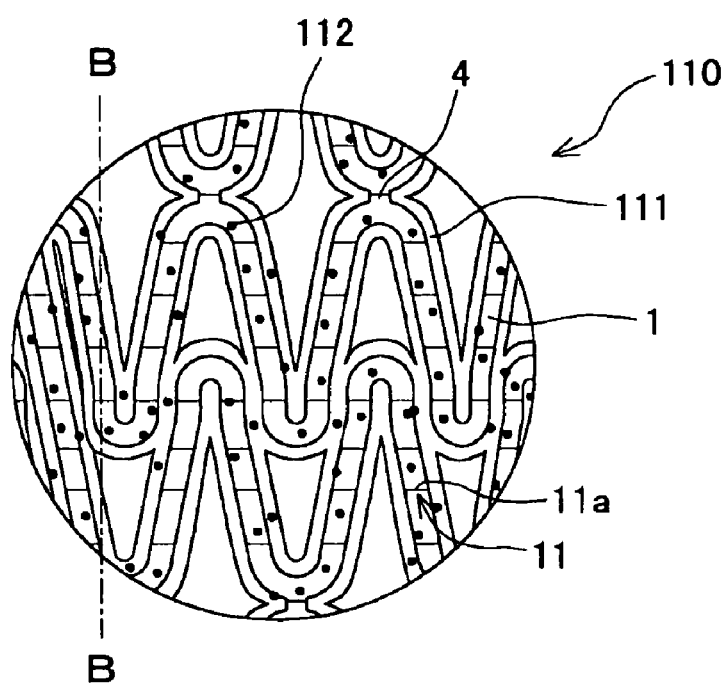
FIG. 15 is a partly enlarged view of the implantable tubular device shown in FIG. 14.
Figure 16:
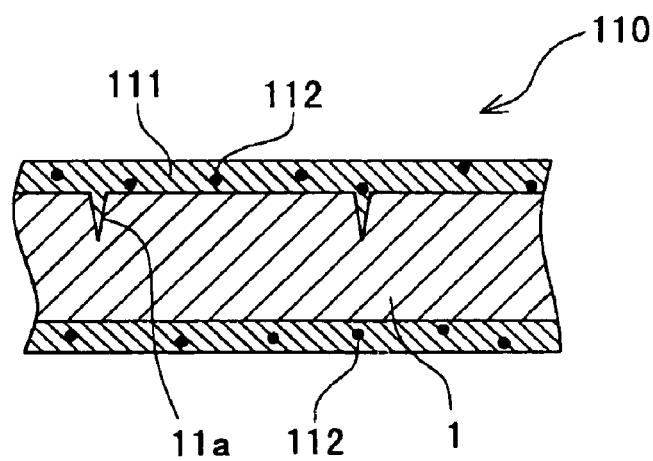
FIG. 16 is a sectional view taken along a line B-B of FIG. 15.

FIG. 14 is a front view of an implantable device according to still another embodiment of the present invention. FIG. 15 is a partly enlarged view of the implantable tubular device shown in FIG. 14. FIG. 16 is a sectional view taken along a line B-B of FIG. 15.

The implantable tubular device can carry the following medicines: medicine for preventing intimal hyperplasia, carcinostatic agent, immunosuppressor, antibiotic, antirheumatic, antithrombotic drug, HMG-CoA reductase inhibitor, ACE inhibitor, calcium antagonist, anti-hyperlipidemia agent, anti-inflammatory agent, integrins inhibitor, antiallergic agent, antioxidant, GP II b III a antagonist, retinoids, flavonoids, carotenoids, lipid-improving agent, DNA-synthesis inhibitor, tyrosine kinase inhibitor, antiplatelet agent, vascular smooth muscle cell proliferution inhibitor, bioprosthetic material(in other words, material originated inorganism), interferon, and epithelial cell formed by genetic engineering. Mixtures each containing two or more of these agents may be used.

The following carcinostatic agents are preferable: vincristine, vinblastine, vindesine, vindesine sulfate, irinotecan, irinotecan hydrochloride, pirarubicin, pirarubicin hydrochloride, paclitaxel(PTX), docetaxel, docetaxel hydrate, and methotrexate(MTX).

The following immunosuppressors are preferable: sirolimus, tacrolimus, tacrolimus hydrate, azathioprine(AZP), ciclosporin(CYA), cyclophosphamide, mycophenolate mofetil, gusperimus hydrochloride, and mizoribine.

The following antibiotics are preferable: mitomycin, adriamycin(ADM), doxorubicin, doxorubicin hydrochloride (DXR), actinomycin, actinomycin D, daunorubicin, daunorubicin hydrochloride, idarubicin, idarubicin hydrochloride (DNR), pirarubicin, pirarubicin hydrochloride(THP), aclarubicinn, aclarubicin hydrochloride(ACR), epirubicin, epirubicin =hydrochloride(EPI), peplomycin, peplomycin sulfate(PEP), and zinostatin stimalamer.

The following antirheumatics are preferable: methotrexate (MTX), sodium thiomalate, penicillamine, and lobenzarit, lobenzarit disodium.

The following anti-thrombotic drugs are preferable: heparin, aspirin, antithrombin preparation, ticlopidine, ticlopidine hydrochloride and hirudin.

The following HMG-CoA reductase inhibitors are preferable: cerivastatin, cerivastatin sodium, atorvastatin, atorvastatin calcium, nisvastatin, itavastatin, fluvastatin, fluvastatin sodium, simvastatin, lovastatin, and pravastatin, pravastatin sodium.

The following ACE inhibitors are preferable: quinapril, quinapril hydrochloride, perindopril erbumine, trandolapril, cilazapril, temocapril, temocapril hydrochloride, delapril, delapril hydrochloride, enalapril maleate, lisinopril, and captopril.

The following calcium antagonists are preferable: nifedipine, nilvadipine, diltiazem, diltiazem hydrochloride, benidipine, benidipine hydrochloride, and nisoldipine.

As the cholesterol-lowering agent, probucol is preferable.

As the antiallergic agents, tranilast is preferable.

As the retinoids, all trans retinoic acid is preferable.

As the flavonoids and carotenoids, catechins is preferable. Particularly, Epigallocatechin gallate, anthocyanins, proanthocyanidin, lycopene, and β-carotin are preferable.

As the tyrosine kinase inhibitors, genistein, erbstatin, and Tyrphostins are preferable.

As the anti-inflammatory agents, steroids such as dexamethasone and prednisolone are preferable.

The following bioprosthetic materials(in other words, materials originated inorganism) are preferable: EGF (epidermal growth factor), VEGF (vascular endothelial growth factor), HGF (hepatocyte growth factor), PDGF (platelet derived growth factor), and bFGF (basic fibroblast growth factor).

An implantable device 110 shown in FIGS. 14 through 16 has the coating material 111 coating the outer surface including the outer surface of the deformable portion 11 of the body 1 of the device and the inner surface of the body 1 thereof. The coating material contains the medicine or the bioprosthetic material(in other words, material originated inorganism) or has the medicine or the bioprosthetic material on its surface. The implantable tubular device 110 of the embodiment has the coating material 111 made of a mixture of a medicine 112. As the material for the coating material, those described above can be used. In the implantable tubular device 110 of the embodiment, as shown in FIG. 15, the coating material-forming material is in penetration into the groove 11a forming the deformable portion 11. The penetration of the coating material-forming material into the groove 11a allows the deformable portion to be reinforced without preventing a large amount of deformation of the deformable portion and also allows the coating material to adhere to the body 1 of the device firmly. Thus it is possible to prevent the coating material from separating from the body 1. Furthermore because the portion of the coating material 111 into which the coating material-forming material penetrates is thicker than other portions of the coating material 111. Therefore, if the body 1 of the implantable tubular device is broken at the deformable portion 11 (groove 11a) in an implanting operation, the coating member is hardly broken. Thus even though the deformable portion ii is broken, it is possible to prevent a broken portion from separating from the body 1.

As shown in FIG. 15, the implantable tubular device 110 of the embodiment has the coating material 111, composed of a mixture of the biodegradable material and the medicine 112, coating the inner and outer surfaces thereof. After the implantable tubular device is implanted in the human body, the biodegradable material decomposes and the medicine is gradually discharged from the coating material. Thereby the effect of the medicine can be obtained continuously for a certain period of time.

The medicine or the bioprosthetic material(in other words, material originated inorganism) is carried by the body of the implantable tubular device by preparing a mixed solution containing a solvent which can disperse the medicine or the bioprosthetic material(in other words, material originated inorganism) therein without modifying them and which has adherence to the body of the implantable tubular device; and bringing a portion of the body of the implantable tubular device on which the medicine or the bioprosthetic material(in other words, material originated inorganism) is to be carried into contact with the mixed solution. The body of the implantable tubular device can be brought into contact with the mixed solution by immersing the body thereof in the mixed solution or applying the mixed solution to the body thereof.

Figure 17:
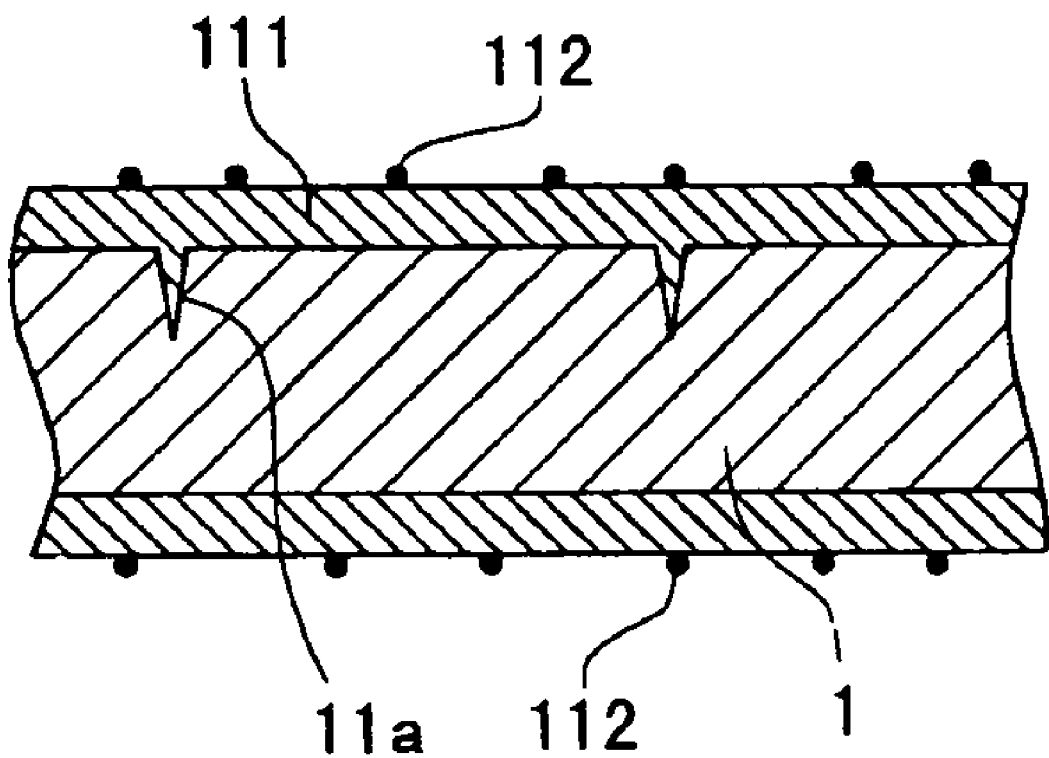
FIG. 17 is an explanatory view for describing an implantable tubular device according to still another embodiment of the present invention.

As shown in FIG. 17, the implantable tubular device may have the coating material 111 made of the biocompatible material, the biodegradable material or the synthetic resin formed on its surface and further the medicine 112 or the bioprosthetic material(in other words, material originated inorganism) held on the surface of the coating material 111.

The implantable tubular device can have the coating material 111 made of the biocompatible material, the biodegradable material or the synthetic resin on its surface and carries the medicine 112 or the bioprosthetic material(in other words, material originated inorganism) on the surface of the coating material 111 as follows:

Initially, the coating material is formed on the body of the implantable tubular device by preparing a solution in which a solvent dissolving a coating material-forming material therein without modifying it, bringing a portion of the body of the implantable tubular device on which the coating material is to be formed into contact with the solution, and removing the solvent. The body of the implantable tubular device can be brought into contact with the solution by immersing the body thereof in the solution or applying the solution to the body thereof. Then, in the case where the medicine or the bioprosthetic material(in other words, material originated inorganism) has adhesion to the coating material, a solution consisting of water in which the medicine or the bioprosthetic material(in other words, material originated inorganism) is dissolved or dispersed is prepared. In the case where the medicine or the bioprosthetic material(in other words, material originated inorganism) does not have adhesion to the coating material, the medicine or the bioprosthetic material (in other words, material originated inorganism) is added to a solution containing a material which can disperse the medicine or the bioprosthetic material(in other words, material originated inorganism) and which has adhesion to the coating material to form a mixed solution. Then, a portion of the body of the implantable tubular device on which the medicine or the bioprosthetic material(in other words, material originated inorganism) is to be held is brought into contact with the mixed solution. The body of the implantable tubular device can be brought into contact with the mixed solution by immersing the body thereof in the mixed solution or applying the mixed solution to the body thereof.

EXAMPLE

Example 1

Grooves were formed on the entire peripheral surface of a pipe made of SUS 316L having a diameter of 1.44 mm, a thickness of 0.095 mm by utilizing a laser machining method (YAG laser model SL116E manufactured by NEC). The interval between the adjacent spiral grooves was 0.1 mm. The depth of the groove was about 0.02 mm. In the laser machining method, the output of the laser was 2.35 kW, and the processing speed was 50 mm/mimute.

The metal pipe having the spiral groove formed on its surface was mounted on a jig equipped with a rotating motor and a fastening mechanism to prevent run-out of the metal pipe. The jig was set on a numerically controllable XY table. The XY table and the rotating motor were connected to a personal computer such that an output of the personal computer was transmitted to a numerical controller of the XY table and the rotating motor. A development drawing representing the stent having the structure shown in FIG. 2 was inputted to the personal computer storing a design software.

The XY table and the rotating motor were driven in accordance with design data outputted from the personal computer. The pipe was irradiated with a laser beam to machine the pipe into a stent structure having the configuration shown in FIG. 1.

As the laser machining condition for the metal pipe, current value was 25 A, an output was 1.5 W, and a drive speed was 10 mm/min. The machine is not limited to the above-described system but it is possible to use a laser marker of the galvanometer system to be driven by a laser machining device.

A stent structure having the configuration shown in FIG. 1 was prepared in this manner. The stent structure was dipped in a stainless steel chemical polishing solution at about 98° C. for about 10 minutes to chamfer and chemically polish the stent structure. The chemical polishing solution used in example 1 contained a mixture of hydrochloric acid and nitric acid serving as a main component, an organic sulfur compound, and a surface active agent. The chemical polishing solution is commercially available as Sunbit 505 from Sanshin Chemical Industry K.K.

Figure 3:
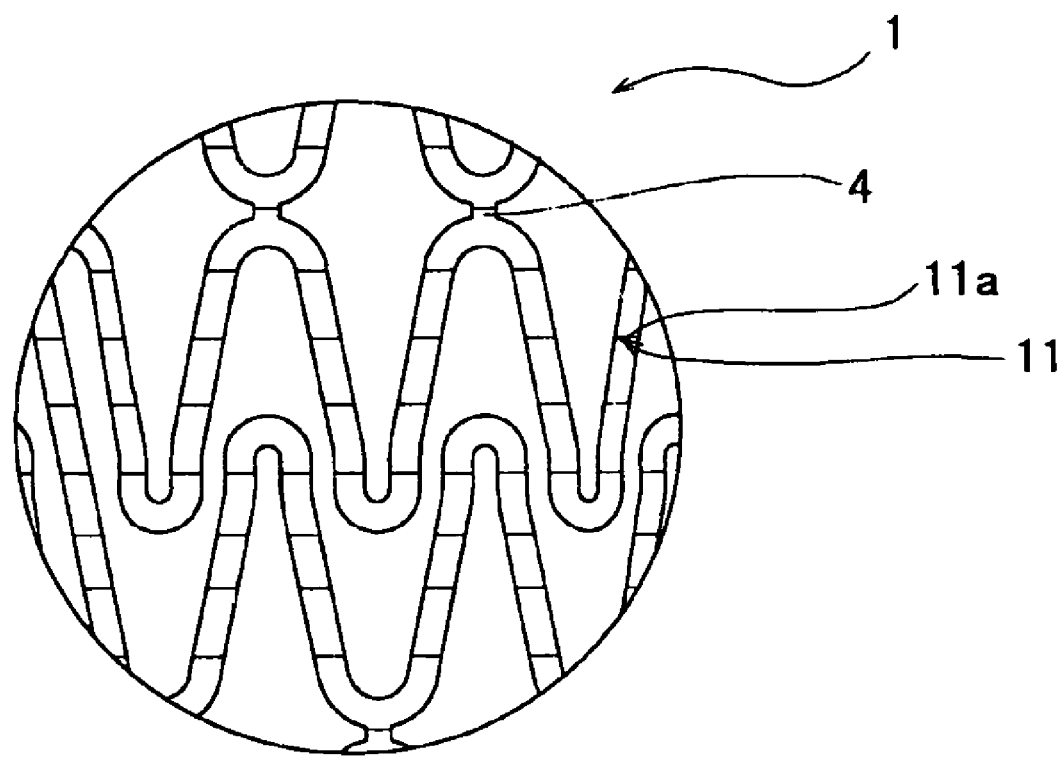
FIG. 3 is a partly enlarged front view of the implantable tubular device of FIG. 1.

In this manner, the stent of the present invention having the configuration shown in FIGS. 1 through 3 was prepared. The stent had an entire length of 20 mm and an outer diameter of 1.4 mm. The width of a portion constituting a wavy element (wavy annular member) and a joining portion was 0.12 mm. A connection portion had a width 0.03 mm and a length of 0.1 mm. The stent had a thickness of about 0.08 mm.

Comparison Example

Except a groove was not formed on the pipe, the stent of the comparison example was formed in a way similar to that of the example 1.

Experiment 1

To examine the influence of the groove (deformable portion) on the flexibility of the stent, the following experiments were conducted by using the stent of the example 1 and that of the comparison example.

Figure 9:
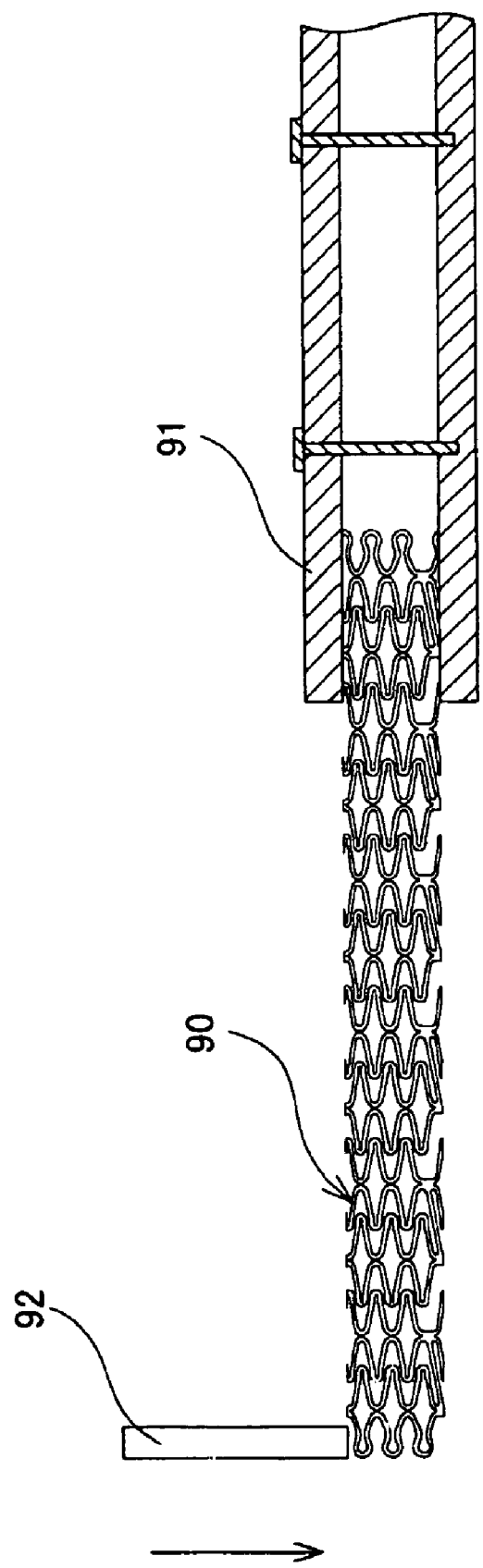
FIG. 9 is an explanatory view for describing a method of measuring flexibility of the implantable tubular device of the present invention.

Referring to FIG. 9, an undilated stent 90 was fixed to a fixing device 91 at a position thereof 10 mm spaced from the rear end thereof. In this state, a portion of the stent 90 in the vicinity of the front end thereof was pressed downward with a penetrator 92 to measure a load applied thereto when the front end thereof descended 2 mm. The results of the measurement are shown in table 1 below.

TABLE 1

|  | Load (g) |
|---|---|
| Example 1 | 0.77 |
| Comparison example | 2.60 |

As shown in table 1, the load of the groove-unprovided stent of the comparison example was 2.60 g, whereas that of the groove-provided stent (example 1) was 0.77 g which was much smaller than 2.60 g. This indicates that owing to the formation of the groove on the stent, the stent is allowed to have a much higher flexibility Example 2

A mixed solution was formed from a solution containing 5 mg of cerivastatin sodium which is an HMG-CoA reductase inhibitor dissolved in 1 ml of ethanol and a solution containing 40 mg of polylactic acid dissolved in 4 ml of dichloromethane. The stent of example 1 was sprayed with the mixed solution of the polylactic acid containing the cerivastatin sodium. That is, the entire outer surface of the stent having the deformable portion was coated with the biodegradable material containing the medicine.

Example 3

A solution containing 40 mg of polylactic acid dissolved in 4 ml of dichloromethane was prepared. The stent of example 1 was immersed in the solution. After the stent was pulled upward, it was dried. The stent coated with the polylactic acid was prepared. That is, the entire surface of the stent having the deformable portion was coated with the biodegradable material.

Example 4

A mixed solution containing 5 mg of EGF which was used as a bioprosthetic material(in other words, material originated inorganism) and 40 mg of gelatin dissolved in 4 ml of water was prepared. The stent of example 1 was sprayed with the mixed solution of the gelatin containing the EGF. That is, the entire outer surface of the stent having the deformable portion was coated with the biodegradable material containing the bioprosthetic material(in other words, material originated inorganism).

Example 5

5 mg of paclitaxel(PTX) which is a carcinostatic agent and 40 mg of silicone were dissolved in 4 ml of cyclohexane. The stent of example 1 was sprayed with the solution of the silicone containing the paclitaxel. That is, the entire outer surface of the stent having the deformable portion was coated with the biocompatible material containing the medicine.

Example 6

A solution containing 40 mg of silicone dissolved in 4 ml of cyclohexane was prepared. The stent of example 1 was immersed in the solution. After the stent was pulled upward, it was dried. That is, the stent coated with the silicone was prepared. The surface of the stent was sprayed with a solution containing 5 mg of cerivastatin sodium dissolved in 1 ml of ethanol. The surface of the stent coated with the silicone was coated with the cerivastatin sodium. That is, the entire outer surface of the stent having the deformable portion was coated with the biocompatible material coated with the medicine.

Experiment 2

To examine the influence of the groove (deformable portion) on the flexibility of the stent, the following experiments were conducted by using the stent of the example 2 through 6 and that of the comparison example.

Referring to FIG. 9, an undilated stent 90 was fixed to a fixing device 91 at a position thereof 10 mm spaced from the rear end thereof. In this state, a portion of the stent 90 in the vicinity of the front end thereof was pressed downward with a penetrator 92 to measure a load applied thereto when the front end thereof descended 2 mm. The results of the measurement are shown in table 2 below.

TABLE 2

|  | Load (g) |
|---|---|
| Example 2 | 1.83 |
| Example 3 | 1.79 |

TABLE 2-continued

| | Load (g) |
|---|---|
| Example 4 | 1.67 |
| Example 5 | 2.03 |
| Example 6 | 2.00 |
| Comparison example | 2.60 |

Although some preferred embodiments have been described, many modifications and variations may be made thereto in the light of the above teachings. It is therefore to be understood that within the scope of the appended claims, the invention may be practiced otherwise than as specifically described.

What is claimed is:

1. An implantable tubular device formed substantially tubular and having a deformable portion formed on a peripheral surface thereof and including wavy annular members with bent portions, with said deformable portion forming a predetermined angle with respect to an axial direction of said device and when the deformable portion is prolonged it forms an endless annular configuration, said deformable portion being easy to deform in comparison with a remainder part of said device, said deformable portion being formed in a plural number, and, said deformable portions being formed as grooves having a bottom surface provided on an inner surface of said tubular device which faces inwardly toward an interior of said tubular device, on an outer surface of said tubular device which faces away from the interior of the tubular device or on both the inner and outer surfaces of said tubular device, and the deformable portions being formed on the bent portions of the wavy annular members such that the deformable portions are substantially parallel with one another.

2. An implantable device according to claim 1, wherein a depth of said grooves is set to 5-50% of a thickness of said device.

3. An implantable device according to claim 1, wherein said deformable portions form an angle of 20-90° with the axial direction of said device.

4. An implantable device according to claim 1, wherein an interval between said deformable portions in the axial direction of said device is 0.01-1 mm.

5. An implantable device according to claim 1, wherein said device consists of a stent or a stent graft.

6. An implantable device according to claim 1, wherein said device is formed by forming a spiral deformable portion-provided tubular body by connecting axially adjacent coiled wire members to each other directly or indirectly and removing a portion of said tubular body other than a portion thereof which is to be formed as said device.

7. An implantable device according to claim 1, wherein said device is formed by forming an annular deformable portions-provided tubular body by directly or indirectly connecting ring members so disposed parallel to each other as to form a cylindrical shape and removing a portion of said tubular body other than a portion thereof which is to be formed as said device.

8. An implantable device according to claim 1, wherein a depth of said grooves is set to 1-99% of a thickness of said device.

9. An implantable device according to claim 1, wherein said device carries a medicine, a bioprosthetic material or a biosynthesis material.

10. An implantable device according to claim 9, wherein said medicine contains at least one pharmaceutical selected from the group consisting of a medicine for preventing intimal hyperplasia, a carcinostatic agent, an immunosuppressor, an antibiotic, an antirheumatic, an antithrombotic drug, HMG-CoA reductase inhibitor, an ACE inhibitor, a calcium antagonist, an anti-hyperlipidemia agent, anti-inflammatory agent, an integrins inhibitor, an antiallergic agent, an antioxidant, a GP II b III a antagonist, retinoids, flavonoids, carotenoids, a lipid-improving agent, a DNA-synthesis inhibitor, a tyrosine kinase inhibitor, an antiplatelet agent, a vascular smooth muscle cell proliferation inhibitor, an anti-inflammatory agent, a bioprosthetic material and interferon.

11. An implantable device according to claim 1, wherein at least one part of the outer surface of said device is coated with a coating material made of a biocompatible material, a biodegradable material or a synthetic resin.

12. An implantable device according to claim 11, wherein said coating material carries a medicine, a bioprosthetic material or a biosynthesis material.

13. An implantable device according to claim 11, wherein said coating material is formed of a biodegradable material to which a medicine, a bioprosthetic material or a biosynthesis material is added.

14. An implantable device according to claim 1, wherein at least one part of an outer surface of said deformable portions is coated with a coating material made of a biocompatible material, a biodegradable material or a synthetic resin.

15. An implantable device according to claim 1, wherein said device consists of a stent having a frame structure, and said deformable portions are entirely on said frame structure.

16. An implantable device according to claim 1, wherein said deformable portion consists of a groove formed on an inner surface of said device or on an outer surface thereof or on both said inner and outer surfaces thereof.

17. An implantable device according to claim 16, wherein a depth of said groove is set to 5-50% of a thickness of said device.

18. The implantable tubular device of claim 1, wherein the bottom surface of the grooves is formed as a V-shaped bottom surface.

19. An implantable device according to claim 1, wherein said deformable portion entirely includes the bent portions formed on the device.

20. An implantable device according to claim 1, wherein said deformable portions form an angle of 70-90° with an axial direction of the device.

21. An implantable device according to claim 1, wherein an interval spacing between adjacent grooves is 0.01 to 1 mm.

22. An implantable device according to claim 1, wherein said device has a mixture of medicine and biodegradable material applied to the outer surface of the device.

23. An implantable tubular device formed substantially tubular and having a diameter so set that said device can be inserted into a lumen in a human body and capable of dilating radially upon application of a force acting radially outwardly from an interior of said tubular body, said device comprising:
a plurality of annular members arranged in an axial direction of said device, the annular members including a plurality of bent portions; and
connection portions each connecting said annular members to each other in the axial direction of said device;
wherein each of said annular members has deformable portions forming a predetermined angle with respect to the axial direction of the device, and when a deformable portion is prolonged it forms a spiral configuration, and said deformable portions being more easily deformed than a remainder of the device, said deformable portions being formed as grooves having a bottom surface provided on an inner surface of the tubular device which faces inwardly toward an interior of the tubular device, on an outer surface of the tubular device which faces away from the interior of the tubular device or on both the inner and outer surfaces of the tubular device, and a plurality of the deformable portions are located on each of the plurality of bent portions.

24. The implantable tubular device of claim 23, wherein the bottom surface of the grooves is formed as a V-shaped bottom surface.

25. An implantable device according to claim 23, wherein said deformable portion entirely includes the bent portions formed on the device.

26. An implantable device according to claim 23, wherein said deformable portions form an angle of 70-90° with an axial direction of the device.

27. An implantable device according to claim 23, wherein an interval spacing between adjacent grooves is 0.01 to 1 mm.

28. An implantable device according to claim 23, wherein said device has a mixture of medicine and biodegradable material applied to the outer surface of the device.

29. An implantable tubular device having a plurality of deformable portions formed on a peripheral surface of the tubular device, with the deformable portions forming a predetermined angle with respect to an axial direction of the tubular device, and when one of the deformable portions is prolonged it forms an endless annular configuration, and said deformable portions being more easily deformed in comparison with a remainder part of the tubular device, the tubular device being comprised of a plurality of annular units, with adjacent annular units connected together by joining portions, the annular units each being comprised of at least one wavy annular member including a bent portion, said deformable portions being formed as grooves having a bottom surface provided on one of an inner surface of said tubular device which faces inwardly toward an interior of said tubular device, and an outer surface of said tubular device which faces away from the interior of the tubular device, and the deformable portions formed on the bent portions of the wavy annular members such that the deformable portions are substantially parallel with one another.

30. An implantable device according to claim 29, wherein the grooves are provided on an inner surface of said tubular device which faces inwardly toward an interior of the tubular device, on an outer surface of the tubular device which faces away from the interior of the tubular device or on both the inner and outer surfaces of the tubular device.

31. The implantable tubular device of claim 29, wherein the bottom surface of the grooves is formed as a V-shaped bottom surface.

* * * * *